(12) United States Patent
Koyama

(10) Patent No.: US 9,111,437 B2
(45) Date of Patent: Aug. 18, 2015

(54) ELECTRONIC DEVICE, METHOD OF EXTRACTING DATA AND PROGRAM

(71) Applicant: SEIKO INSTRUMENTS INC., Chiba (JP)

(72) Inventor: Kazuhiro Koyama, Chiba (JP)

(73) Assignee: SEIKO INSTRUMENTS INC. (JP)

( * ) Notice: Subject to any disclaimer, the term of this patent is extended or adjusted under 35 U.S.C. 154(b) by 102 days.

(21) Appl. No.: 14/062,028

(22) Filed: Oct. 24, 2013

(65) Prior Publication Data

US 2014/0118124 A1  May 1, 2014

(30) Foreign Application Priority Data

Oct. 30, 2012 (JP) ................................ 2012-239492
Aug. 19, 2013 (JP) ................................ 2013-169921

(51) Int. Cl.
G08B 1/00 (2006.01)
G08C 19/00 (2006.01)
A61B 5/00 (2006.01)
A61B 5/024 (2006.01)

(52) U.S. Cl.
CPC ............ *G08C 19/00* (2013.01); *A61B 5/02438* (2013.01); *A61B 5/7232* (2013.01); *A61B 5/0015* (2013.01); *A61B 5/681* (2013.01); *A61B 5/6823* (2013.01)

(58) Field of Classification Search
CPC .... G08B 21/0453; G08B 21/24; G08B 21/22; G08B 21/0288; G08B 21/0446; G08C 19/00; G06F 19/3462; A61B 5/7232; A61B 5/02438; A61B 5/0015; A61B 5/6832; A61B 5/681; A61J 7/0481; A61J 2007/0418; A61J 2007/0436

USPC ......... 340/309.16, 573.1, 539.12, 521, 539.1, 340/539.11, 517; 600/509, 513, 300, 301, 600/528, 483, 484, 485, 503; 368/10
See application file for complete search history.

(56) References Cited

U.S. PATENT DOCUMENTS

| | | | |
|---|---|---|---|
| 7,643,873 B2 * | 1/2010 | Chan .............................. | 600/520 |
| 8,046,058 B2 * | 10/2011 | Lin et al. ........................ | 600/509 |
| 8,125,331 B2 * | 2/2012 | Allen et al. ............... | 340/539.12 |
| 8,797,167 B2 * | 8/2014 | Bangera et al. ............ | 340/573.1 |
| 2007/0159321 A1 * | 7/2007 | Ogata et al. ............... | 340/539.12 |

OTHER PUBLICATIONS

Patent Abstracts of Japan, Publication No. 09-079871, Publication Date Mar. 28, 1997.

* cited by examiner

*Primary Examiner* — Anh V La
(74) *Attorney, Agent, or Firm* — Adams & Wilks

(57) ABSTRACT

A time interval setting unit sets a time interval that depends on the number of items of data stored by a storage unit. A storage processing unit stores the data in the storage unit at every time interval that is set by the time interval setting unit. The storage unit retains the data at the time interval that depends on data acquirement time. A data extraction unit extracts the data by the number of items of data that depends on the number of items of display data, from the items of data stored by the storage unit. When the time interval setting unit updates the time interval, it is not necessary to perform subsampling or compression on the data stored by the storage unit and the data can be retained at the time interval that depends on the data acquirement time with less processing load.

20 Claims, 11 Drawing Sheets

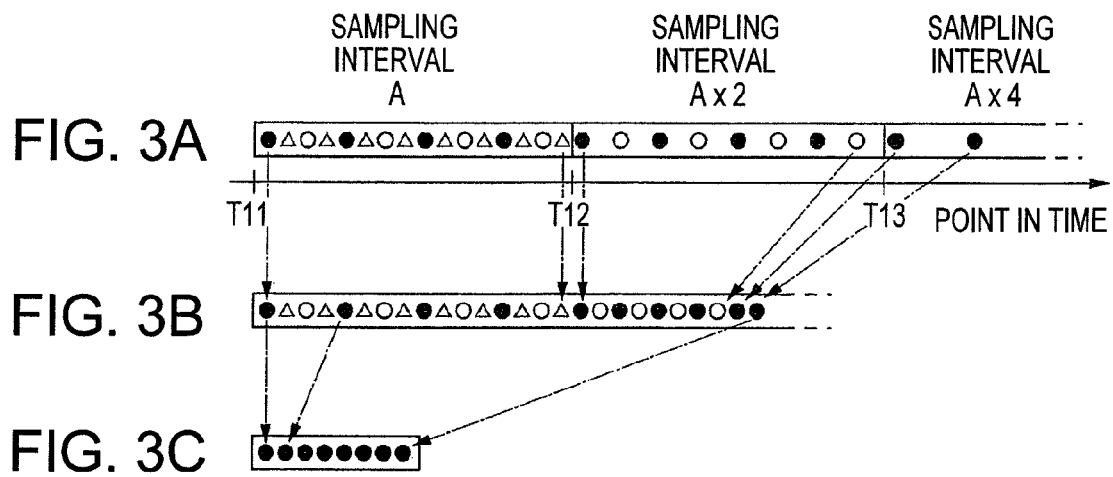
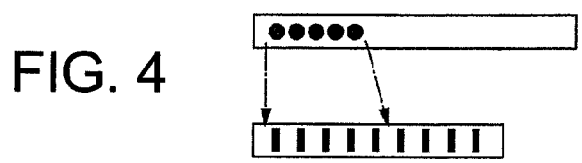
FIG. 4
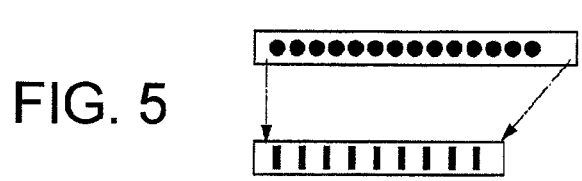
FIG. 5
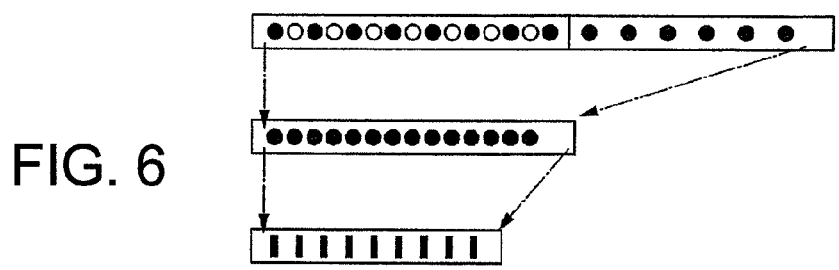
FIG. 6

FIG. 11

| TIME INTERVAL (SECONDS) | NUMBER OF ITEMS OF DATA | TIME (SECONDS) | DATA ACQUISITION TIME (SECONDS) | DATA ACQUISITION TIME (HOURS/MINUTES/SECONDS) | TOTAL NUMBER OF ITEMS OF DATA | STORAGE CAPACITY (BYTE) |
|---|---|---|---|---|---|---|
| 2 | 64 | 128 | 128 | 0 HOURS 2 MINUTES 8 SECONDS | 64 | 640 |
| 4 | 32 | 128 | 256 | 0 HOURS 4 MINUTES 16 SECONDS | 96 | 960 |
| 8 | 32 | 256 | 512 | 0 HOURS 8 MINUTES 32 SECONDS | 128 | 1280 |
| 16 | 32 | 512 | 1024 | 0 HOURS 17 MINUTES 4 SECONDS | 160 | 1600 |
| 32 | 32 | 1024 | 2048 | 0 HOURS 34 MINUTES 8 SECONDS | 192 | 1920 |
| 64 | 32 | 2048 | 4096 | 1 HOURS 8 MINUTES 16 SECONDS | 224 | 2240 |
| 128 | 32 | 4096 | 8192 | 2 HOURS 16 MINUTES 32 SECONDS | 256 | 2560 |
| 256 | 32 | 8192 | 16384 | 4 HOURS 33 MINUTES 4 SECONDS | 288 | 2880 |
| 512 | 32 | 16384 | 32768 | 9 HOURS 6 MINUTES 8 SECONDS | 320 | 3200 |
| 1024 | 32 | 32768 | 65536 | 18 HOURS 12 MINUTES 16 SECONDS | 352 | 3520 |
| 2048 | 32 | 65536 | 131072 | 36 HOURS 24 MINUTES 32 SECONDS | 384 | 3840 ← L11 |
| 4096 | 32 | 131072 | 262144 | 72 HOURS 49 MINUTES 4 SECONDS | 416 | 4160 ← L12 |
| 8192 | 32 | 262144 | 524288 | 145 HOURS 38 MINUTES 8 SECONDS | 448 | 4480 |

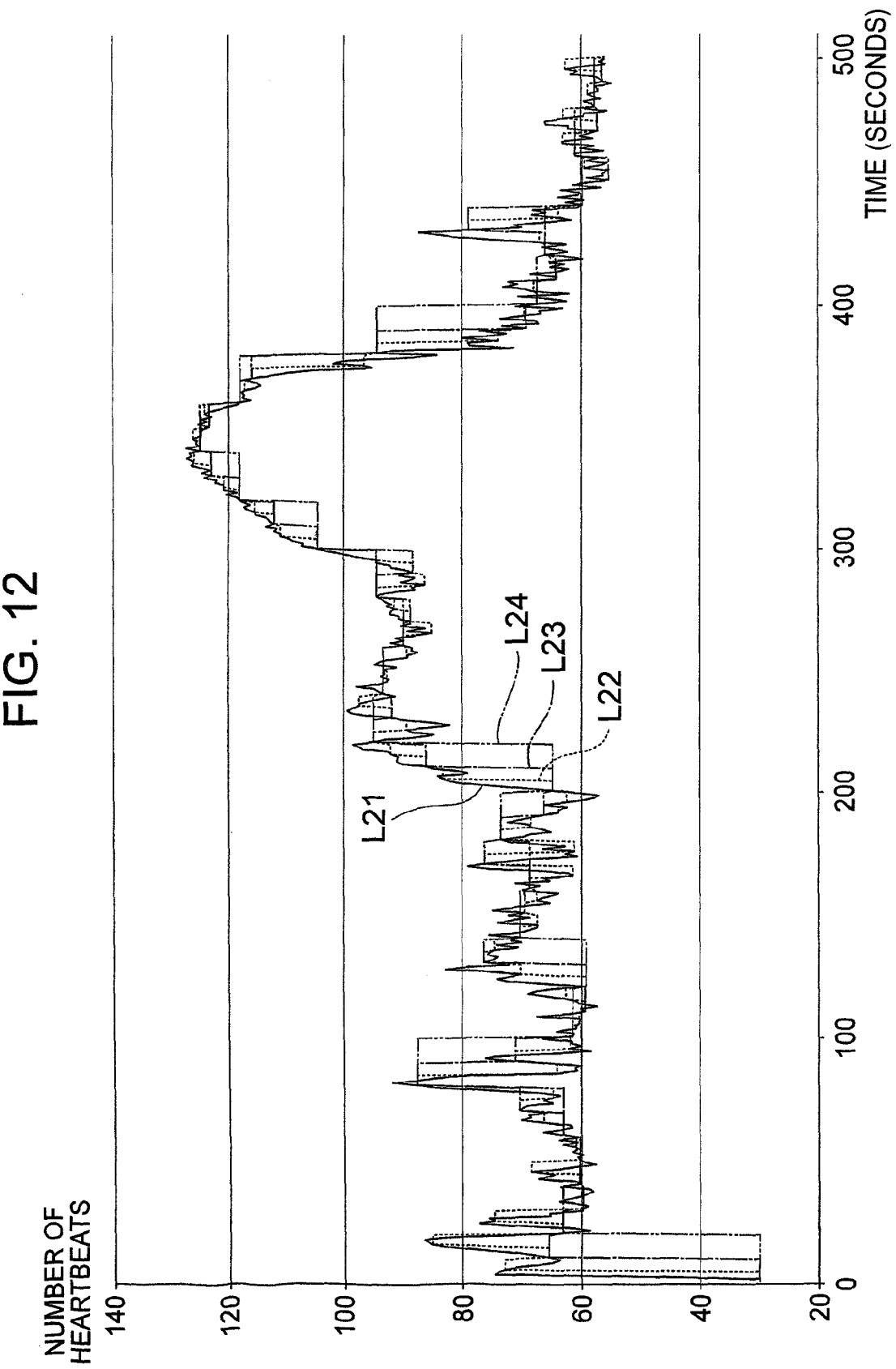

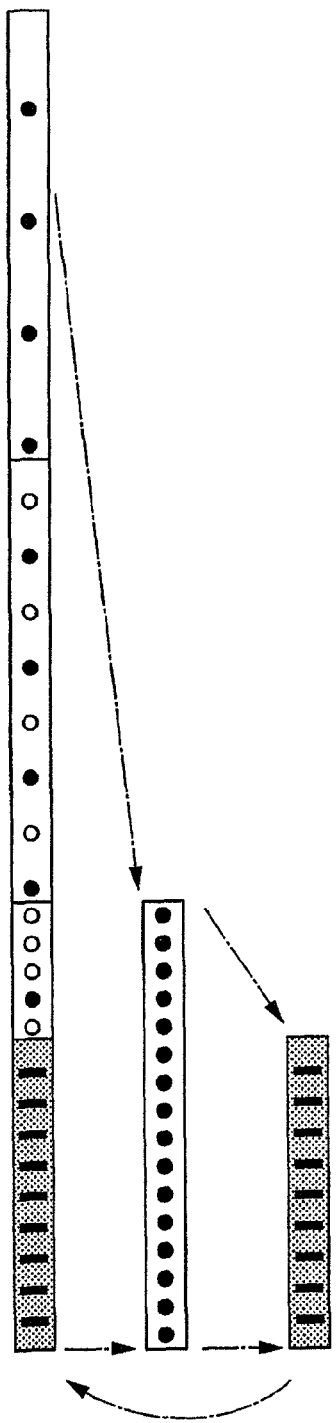
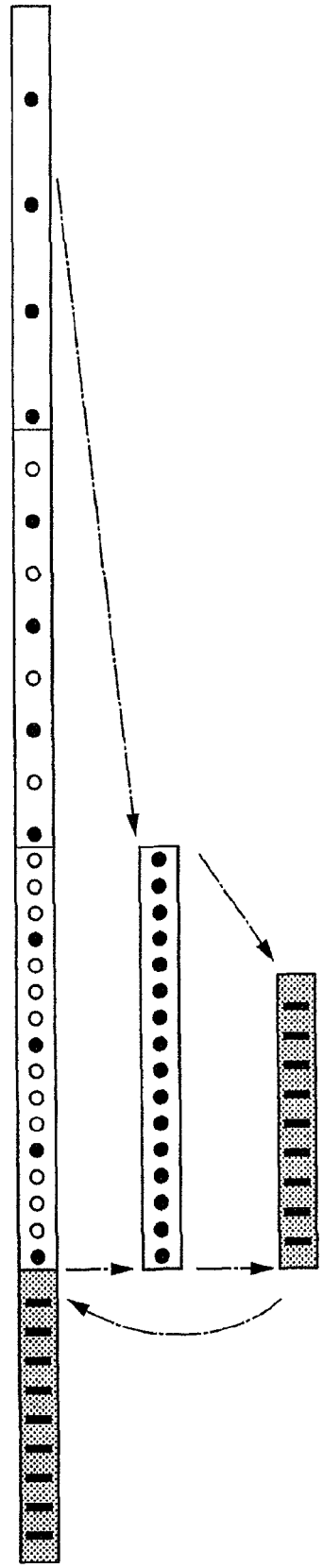
FIG. 15A
FIG. 15B

ELECTRONIC DEVICE, METHOD OF EXTRACTING DATA AND PROGRAM

BACKGROUND OF THE INVENTION

1. Field of the Invention

The present invention relates to an electronic device, a method of extracting data, and a program.

2. Background Art

There is an electronic device that acquires data at every fixed sampling period that is set by a user, as one electronic device that periodically acquires the data, such as a running watch that measures and memorizes living-body information, or a car navigation system that determines current positioning and retains history of the positioning.

On the other hand, in Japanese Patent No. 03415971, a measurement device is disclosed that can retain data at a time interval that depends on data acquirement time. In the measurement device disclosed in Japanese Patent No. 03415971, a result of measurement such as the number of heartbeats is compressed into data with two or more different compression ratios with respect to time and the compressed data is stored in a compressed-data storage unit that corresponds to the compressed data, and a display control unit displays changes in the result of measurement over time on a display unit, based on the compressed data stored in a compressed-data storage unit that has the largest number of items of data.

Accordingly, in the measurement device disclosed in Japanese Patent No. 03415971, although the display device is not enlarged, the changes in the result of measurement over time can be properly displayed regardless of whether measurement time is long or short.

However, in the electronic device that acquires the data at every fixed sampling period, if data acquirement time is long, a memory capacity is exceeded in the process. Thus, the subsequent data cannot be retained or the data needs to be removed in chronological order in which the data is stored. Because of this, the user cannot grasp a trend of the data over the data acquirement time.

In contrast, because the data can be retained at the time interval that depends on the data acquirement time in the measurement device disclosed in Japanese Patent No. 03415971, the user can grasp the tendency of the data over the data acquirement time. However, in the measurement device disclosed in Japanese Patent No. 03415971, processing load is increased in that the result of measurement is compressed into the data with the two or more different compression ratios with respect to time. If the processing load can be reduced, the electronic device (the measurement device in Japanese Patent No. 03415971) can be made smaller in size, and a production cost or an operational cost can be reduced.

SUMMARY OF THE INVENTION

It is an aspect of the present application to provide an electronic device, a method of extracting data, and a program, in all of which data can be retained at a time interval that depends on data acquirement time with less processing load.

According to the present application, there is provided an electronic device including a data acquisition unit that acquires data periodically, a storage unit that stores at least one part of the items of data acquired by the data acquisition unit, a time interval setting unit that sets a time interval that depends on the number of items of data stored by the storage unit, a storage processing unit that stores the data in the storage unit at every time interval that is set by the time interval setting unit, among the items of data acquired by the data acquisition unit, a data extraction unit that extracts the data by the number of items of data that depends on a predetermined number of items of display data, from the items of data stored by the storage unit, and a display unit that displays the data by the number of items of display data, based on the data extracted by the data extraction unit.

In the electronic device, if the time interval setting unit sets the up-to-date time interval and then the number of items of data that the storage processing unit stores in the storage unit at every up-to-date time interval reaches the predetermined number of items of data, the time interval setting unit may set the time interval as being further increased.

In the electronic device, when the time interval is an initially set time interval, if the number of items of data that the storage processing unit stores in the storage unit at every initially set time interval reaches two times the number of items of display data, the time interval setting unit may reset the time interval to two times the time interval, and when the time interval is the reset time interval, if the number of items of data that the storage processing unit stores in the storage unit at every up-to-date time interval reaches the number of items of display data, the time interval setting unit may reset the time interval to two times the up-to-date time interval.

In the electronic device, the data acquisition unit may acquire the data at the time interval, set by the time interval setting unit, which serves as a sampling period.

According to the present application, there is provided a method of displaying data for use in an electronic device including a storage unit that stores the data, including periodically acquiring the data, setting a time interval that depends on the number of items of data that is stored by the storage unit, storing the data in the storage unit at every time interval that is set in the setting of the time interval, among the items of data acquired in the periodical acquiring of the data, extracting the data by the number of items of data that depends on a predetermined number of items of display data, from the items of data stored by the storage unit, and displaying the data by the number of items of display data, based on the data that is extracted in the extracting of the data.

According to the present application, there is provided a program for causing a computer that controls an electronic device including a storage unit that stores data to execute a process, the process including periodically acquiring the data, setting a time interval that depends on the number of items of data that is stored by the storage unit, storing the data in the storage unit at every time interval that is set in the setting of the time interval, among the items of data acquired in the periodical acquiring of the data, extracting the data by the number of items of data that depends on a predetermined number of items of display data, from the items of data stored by the storage unit, and displaying the data by the number of items of display data, based on the data that is extracted in the extracting of the data.

According to the present application, data can be retained at a time interval that depends on data acquisition time with less processing load.

BRIEF DESCRIPTION OF THE DRAWINGS

FIGS. 3A to 3C are explanatory diagrams, each illustrating an example of data that is stored by a storage unit according to the first embodiment.

FIG. 4 is an explanatory diagram illustrating an example of the data which is extracted by a data extraction unit according to the first embodiment when the number of items of data stored by the storage unit is smaller than the number of items of display data.

FIG. 5 is an explanatory diagram illustrating an example of the data that is extracted by the data extraction unit according to the first embodiment when the number of items of data stored by the storage unit is equal to or greater than the number of items of display data in a state that is maintained before a time interval setting unit resets a time interval.

FIG. 6 is an explanatory diagram illustrating an example of the data that is extracted by the data extraction unit according to the first embodiment in a state where the time interval setting unit resets the time interval one time.

FIG. 11 is an explanatory diagram illustrating an example of a relationship between data acquirement time and storage capacity according to the first embodiment.

FIG. 12 is a graph illustrating a result of the simulation showing the number of heartbeats according to the present embodiment.

FIGS. 15A and 15B are explanatory diagrams, each illustrating the data that is present within a storage region when the data extraction unit stores display data that is displayed on a display unit in the storage unit instead of storing the representative data, according to the second embodiment of the present invention.

DETAILED DESCRIPTION OF THE INVENTION

First Embodiment

Figure 1:
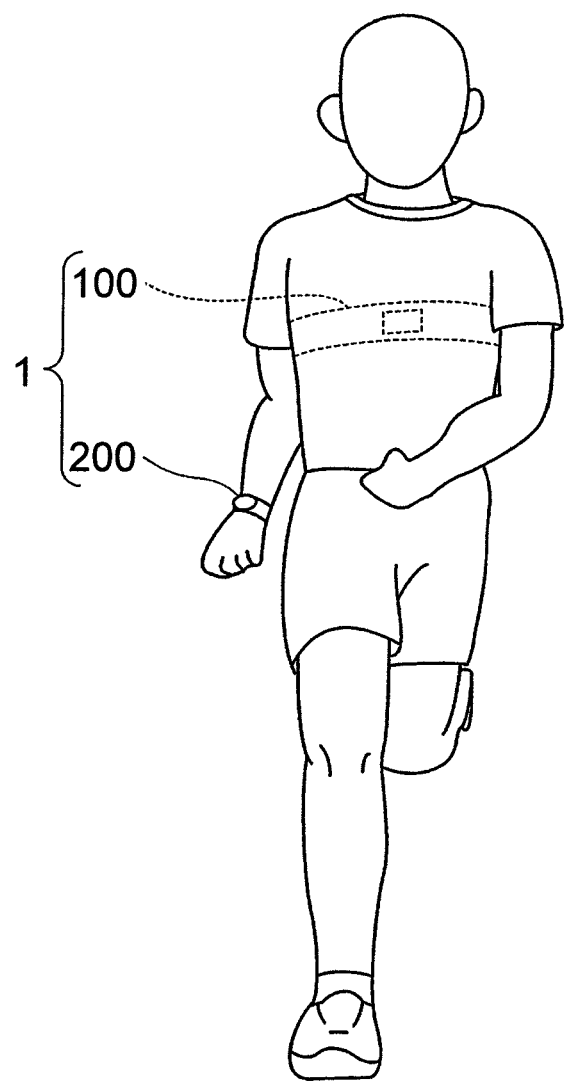
FIG. 1 is a schematic configuration diagram illustrating a system configuration of a running watch system according to a first embodiment of the present invention.

A first embodiment according to the present invention is described below referring to the drawings. FIG. 1 is a schematic configuration diagram illustrating a system configuration of a running watch system according to the first embodiment of the present invention. In FIG. 1, a running watch system 1 includes a chest strap 100 and a running watch 200.

The running watch system 1 provides information such as the number of heartbeats (the number of heartbeats per minute) or lap time to a user who participates in sports such as running.

The chest strap 100, which is attached to a user's chest, detects a user's heartbeat and transmits a heartbeat signal wirelessly to the running watch 200.

The running watch 200 counts the heartbeat signals from the chest strap 100, periodically calculates the number of heartbeats (the number of heartbeats per minute), and stores the result. Then, the running watch 200 displays history of the number of heartbeats, depending on user operation. The running watch 200 corresponds to one example of an electronic device according to the present invention.

However, a range of application of the present invention is not limited to the running watch system. For example, the present invention can be applied to various electronic devices that store information periodically, such as a car navigation system that performs positioning, stores positional information periodically, and displays history of the positional information as a trajectory.

Figure 2:
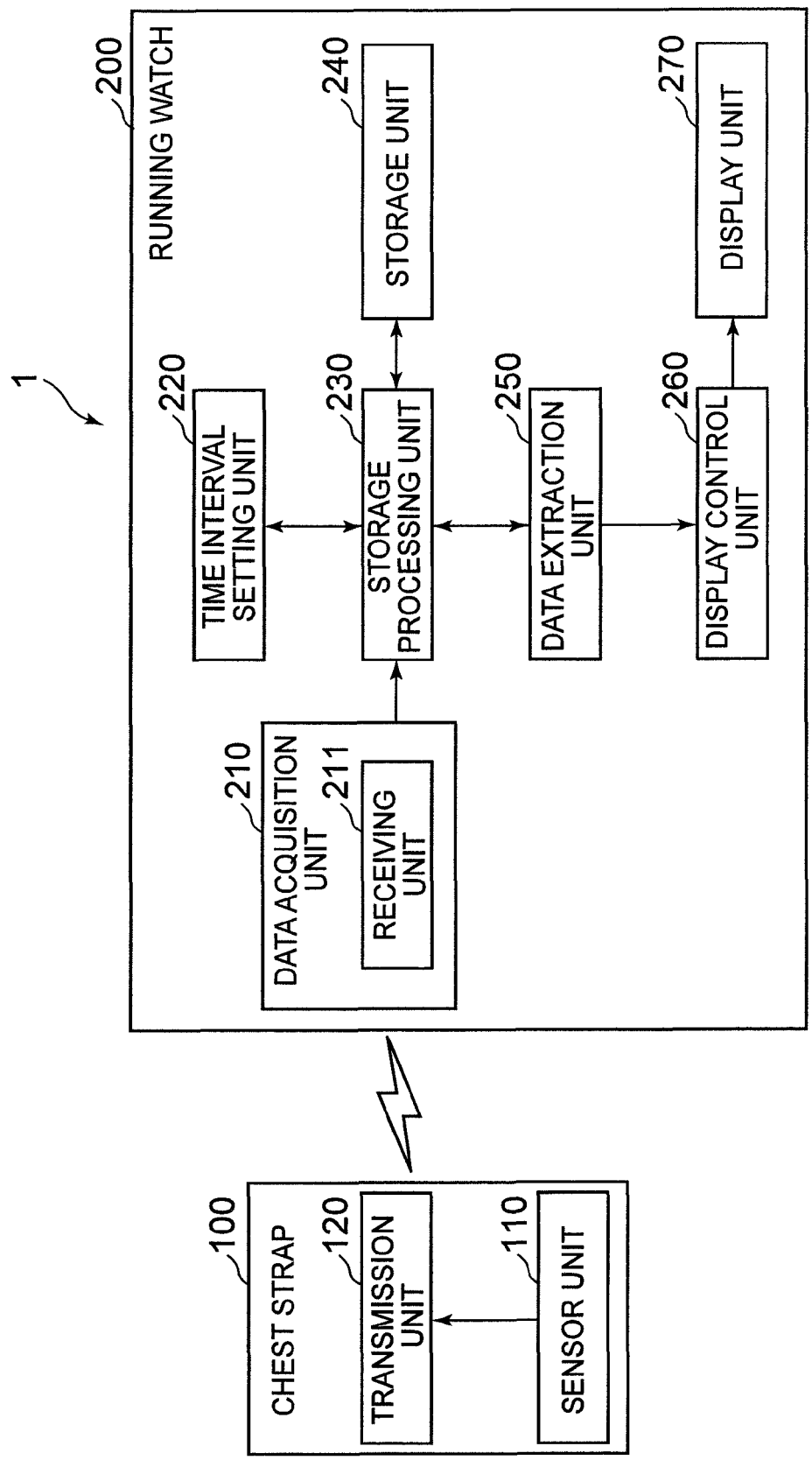
FIG. 2 is a schematic block diagram illustrating a functional configuration of the running watch system according to the first embodiment.

FIG. 2 is a schematic block diagram illustrating a functional configuration of the running watch system. In FIG. 2, the running watch system 1 includes the chest strap 100 and the running watch 200. The chest strap 100 includes a sensor unit 110 and a transmission unit 120. The running watch 200 includes a receiving unit 211, a time interval setting unit 220, a storage processing unit 230, a storage unit 240, a data extraction unit 250, a display control unit 260, and a display unit 270.

The sensor unit 110 has a heartbeat sensor and whenever detecting the heartbeat of the user, outputs the heartbeat signal to the transmission unit 120.

The transmission unit 120 wirelessly transmits the heartbeat signal that is output by the sensor unit 110.

A data acquisition unit 210 acquires data periodically. Particularly, the data acquisition unit 210 acquires the data at the time interval, set by the time interval setting unit 220, which serves as a sampling period.

Specifically, in the data acquisition unit 210, the receiving unit 211 detects the heartbeat signal transmitted by the chest strap 100 (the sensor unit 110). Then, the data acquisition unit 210 counts the heartbeat signals detected by the receiving unit 211, and calculates the number of heartbeats (the number of heartbeats per minute) at every time interval, set by the time interval setting unit 220.

The storage unit 240 stores at least one part of the data acquired by the data acquisition unit 210 according to control by the storage processing unit 230.

The time interval setting unit 220 sets the time interval, depending on the number of items of data stored in the storage unit 240. The time interval is a time interval of the data stored in the storage unit 240 by the storage processing unit 230.

Particularly, if the time interval setting unit 220 itself sets an up-to-date time interval and then the number of items of data that the storage processing unit 230 stores in the storage unit 240 at every up-to-date time interval reaches a predetermined number, the time interval setting unit 220 sets the time interval as being further increased. The up-to-date time interval is one example of the time interval that is set most recently, in the claims. In this manner, the time interval setting unit 220 sets the time interval of the data to be stored in the storage unit 240 as being further increased, depending on an increase in the number of items of data stored by the storage unit 240 and thus alleviates the increase in the number of items of data.

Moreover, when the time interval is the initially set time interval, if the number of items of data that the storage processing unit 230 stores in the storage unit 240 at every initially set time interval reaches two times the number (for example, 32) of items of display data, the time interval setting unit 220 resets the time interval to two times the time interval. The number of items of display data here is defined as a constant number that is set in advance as the number of items of data that the display unit 270 displays on a display screen of the history of the number of heartbeats.

In this manner, the time interval setting unit 220 maintains the initially set time interval and thus stores the items of data the number of which is equal to or more than the number of items of display data, in the storage unit 240. Thus, the display unit 270 can display the data by the number of items of display data. Furthermore, when the time interval setting unit 220 resets the time interval to two times the time interval, the storage unit 240 already stores the items of data with the reset time interval, by the number of items of display data. Therefore, the display unit 270 can display the data by the number of items of display data also after the time interval resetting.

Furthermore, when the time interval is the reset time interval, if the number of items of data that the storage processing unit 230 stores at every up-to-date time interval in the storage unit 240 reaches the number of items of display data, the time interval setting unit 220 resets the time interval to two times the up-to-date time interval. Accordingly, when the time interval setting unit 220 resets the time interval to two times the time interval, the storage unit 240 already stores the items of data with the reset time interval, by the number of items of display data. Therefore, the display unit 270 can display the data by the number of items of display data also after the time interval resetting.

Among the items of data acquired by the data acquisition unit 210, the storage processing unit 230 stores the data in the storage unit 240 at every time interval that is set by the time interval setting unit 220.

The data extraction unit 250 extracts the data by the number of items of data that depends on a predetermined number of display items of data, from the items of data stored by the storage unit 240. For example, the data extraction unit 250 extracts the data by the number of items of display data from the items of data stored by the storage unit 240 and displays the result on the display unit 270.

The display control unit 260 controls the display unit 270 in such a manner that the display unit 270 displays the data.

According to the control by the display control unit 260, the display unit 270 displays the data by the number of items of display data, based on the items of data extracted by the data extraction unit 250. For example, the display unit 270 displays the items of data extracted by the data extraction unit 250, by a graph such as a line graph.

Next, the data stored by the storage unit 240 is described referring to FIGS. 3A to 3C.

FIGS. 3A to 3C are explanatory diagrams, each illustrating an example of the data stored by the storage unit 240. FIG. 3A illustrates an example of timing when the data acquisition unit 210 acquires the data. Furthermore, FIG. 3B illustrates an example of the data stored by the storage unit 240. Furthermore, FIG. 3C illustrates an example of the data displayed by the display unit 270.

In FIGS. 3A to 3C, the data with a sampling period A is indicated by a black circle, a white circle, and a white triangle, the data with the sampling period A×2 is indicated by the black circle and the white circle, and the data with the sampling period A×4 is indicated by the black circle.

In FIG. 3A to 3C, the time interval setting unit 220 initially sets the time interval to A. Therefore, the data acquisition unit 210 acquires the data at the time interval A, which serves as the sampling period, during a period of time from a point in time T11 to a point in time T12, and the storage unit 240 stores the data.

Furthermore, at the point in time T12, the time interval setting unit 220 doubles the time interval and resets the time interval to A×2. Therefore, the data acquisition unit 210 acquires the data at a time interval A×2, which serves as the sampling period, during a period of time from the point in time T12 to a point in time T13. Then, the storage unit 240 stores the data in succession to the data acquired by the data acquisition unit 210 during the period of time from the point in time T11 to the point in time T12.

Furthermore, the time interval setting unit 220 additionally doubles the time interval and resets the time interval to A×4 at the point in time T13. Therefore, the data acquisition unit 210 acquires the data at a time interval A×4, which serves as the sampling period, from the point in time T13 onward. Then, the storage unit 240 stores the data in succession to the data acquired by the data acquisition unit 210 during the period of time from the point in time T12 to the point in time T13.

Accordingly, as illustrated in FIG. 3B, the data stored by the storage unit 240 includes the data with the sampling period A, the data with the sampling period A×2, and the data with the sampling period A×4.

Then, the data extraction unit 250 reads the items of data, at the up-to-date time interval A×4, which serves as the sampling period, by the number of items of display data from the items of data stored by the storage unit 240, and the display unit 270 displays the data.

In this manner, the data extraction unit 250 reads the data with a predetermined sampling period from the items of data stored by the storage unit 240, and therefore the storage unit 240 may store the data with the multiple sampling periods. Therefore, when the time interval setting unit 220 performs the time interval resetting, it is not necessary to perform processing such as subsampling or compression on the data stored by the storage unit 240. In this respect, the load on the running watch 200 can be suppressed.

The data extraction performed by the data extraction unit 250 is described further in detail referring to FIGS. 4 to 7.

FIG. 4 is an explanatory diagram illustrating an example of the data which is extracted by the data extraction unit 250 when the number of items of data stored by the storage unit 240 is smaller than the number of items of display data.

In this case, the data extraction unit 250 reads all the items of data stored by the storage unit 240, and the display control unit 260 causes the display unit 270 to display the items of data.

At that time, the display control unit 260 may cause the display unit 270 to display the data as is (on a scale as is). Alternatively, the display control unit 260 may perform scale conversion such as copying the data and may set the items of data as the number of items of display data in such a manner that the items of data are displayed on the display unit 270.

FIG. 5 is an explanatory diagram illustrating an example of the data that is extracted by the data extraction unit 250 when the number of items of data stored by the storage unit 240 is equal to or greater than the number of items of display data in a state that is maintained before the time interval setting unit 220 resets the time interval.

In this case, the data extraction unit 250 reads the data by the number of items of display data from the items of data stored by the storage unit 240, and the display control unit 260 causes the display unit 270 to display the items of data.

At that time, the data extraction unit 250 divides the time that is obtained by subtracting the sampling point in time of the oldest data from the sampling point in time of the up-to-date data stored by the storage unit 240, by (the number of items of display data—1) and calculates the time interval in a case where the time intervals between the items of display data are equal. Then, the data extraction unit 250 calculates a point in time (the point in time of each display data in a case where the time intervals between the items of display data are equal) that corresponds to each display data, based on the calculated time interval between the items of display data. Then, for every display data, the data extraction unit 250 reads the data at the sampling point in time that is closest to the point in time that corresponds to the display data, as the display data, from the storage unit 240. In this manner, the data extraction unit 250 extracts the data by the number of items of display data from the items of data stored by the storage unit 240 in such a manner that the sampling periods are as equal as possible.

Alternatively, for every display data, the data extraction unit 250 may read one item of data at the sampling point in time that is closest to the point in time that corresponds to the display data before the point in time that corresponds to the display data, and read one item of data at the sampling point in time that is closest to the point in time that corresponds to the display data after the point in time that corresponds to the display data and may set an average value of the two read items of data as a display data value.

FIG. 6 is an explanatory diagram illustrating an example of the data that is extracted by the data extraction unit 250 in a state where the time interval setting unit 220 resets the time interval one time. In FIG. 6, the data the sampling period of which is the time interval (therefore, the time interval that is two times the initially set time interval) that is reset by the time interval setting unit 220 is indicated by a black circle and the other items of data are indicated by a white circle.

In this case, the data extraction unit 250 first extracts the data the sampling period of which is the time interval that is reset by the time interval setting unit 220, from the items of data stored by the storage unit 240.

At this point, the time interval setting unit 220 maintains the initially set time interval until the number of items of data stored by the storage unit 240 reaches two times the number of items of display data. Accordingly, also immediately after two times the initially set time interval is reached, because the items of data with the time interval (the data indicated by the black circle) can be secured by the number of items of display data, a display defect (an occurrence of a display region on which the data is not displayed) can be avoided.

That is, the data extraction unit 250 reads the items of data the number of which is equal to or more than the number of items of display data from the storage unit 240. Subsequently, the data extraction unit 250 reads the data by the number of items of display data, as illustrated in FIG. 5, from the extracted items of data (the items of data, the sampling period of each of which is the time interval that is reset by the time interval setting unit 220), and the display control unit 260 causes the display unit 270 to display the items of data.

In addition, the data extraction unit 250 can use various methods as a method of extracting the data the sampling period of which is the time interval that is reset by the time interval setting unit 220 from the items of data stored by the storage unit 240.

For example, the storage unit 240 first stores the data the sampling period of which is the time interval that is initially set by the time interval setting unit 220, two times the number of items of display data, and subsequently stores the data the sampling period of which is the time interval that is reset by the time interval setting unit 220. Therefore, the data extraction unit 250 can extract the data the sampling period of which is the time interval that is reset by the time interval setting unit 220, based on the order in which the items of data are arranged in the storage unit 240, such as in a case where every other data is extracted beginning with the data that is present when the initially set time interval is at work.

Alternatively, the storage unit 240 may store the data in such a manner that the data is matched to the sampling point in time or the sampling period. In this case, the data acquisition unit 210 can extract the data the sampling period of which is the time interval that is reset by the time interval setting unit 220, based on the sampling point in time or the sampling period that is stored by the storage unit 240.

In addition, the data extraction unit 250 may read the data at the sampling point in time that is closest to the point in time that corresponds to the display data, from the storage unit 240, as illustrated in FIG. 5, for every display data, with all the items of data stored in the storage unit 240 being targets for reading.

Figure 7:
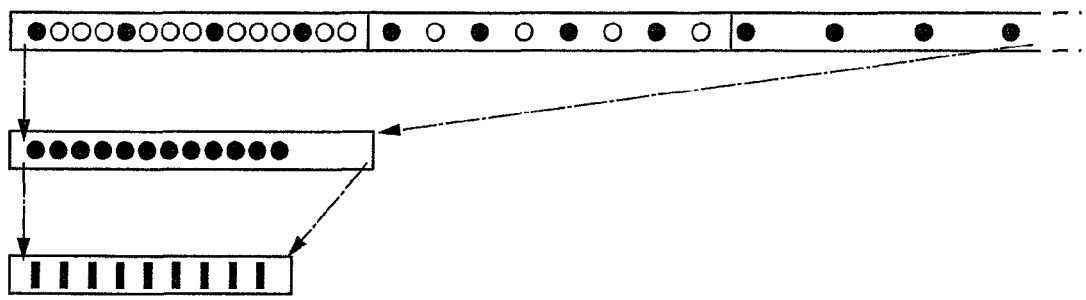
FIG. 7 is an explanatory diagram illustrating an example of the data that is extracted by the data extraction unit according to the first embodiment in a state where the time interval setting unit resets the time interval two times.

FIG. 7 is an explanatory diagram illustrating an example of the data that is extracted by the data extraction unit 250 in a state where the time interval setting unit 220 performs the time interval resetting two times. In FIG. 7, the data the sampling period of which is the up-to-date time interval (therefore, the time interval that is four times the initially set time interval) that is reset by the time interval setting unit 220 is indicated by a black circle and the other items of data are indicated by a white circle.

Also in this case, as illustrated in FIG. 6, the data extraction unit 250 first extracts the data the sampling period of which is the up-to-date time interval that is set by the time interval setting unit 220, from the items of data stored by the storage unit 240. Then, the data extraction unit 250 reads the data by the number of items of display data from the extracted items of data, and the display control unit 260 causes the display unit 270 to display the items.

In addition, the data extraction unit 250 may read the data at the sampling point in time that is closest to the point in time that corresponds to the display data, from the storage unit 240, as illustrated in FIG. 5, for every display data, with all the items of data stored in the storage unit 240 being targets for reading.

Figure 8:
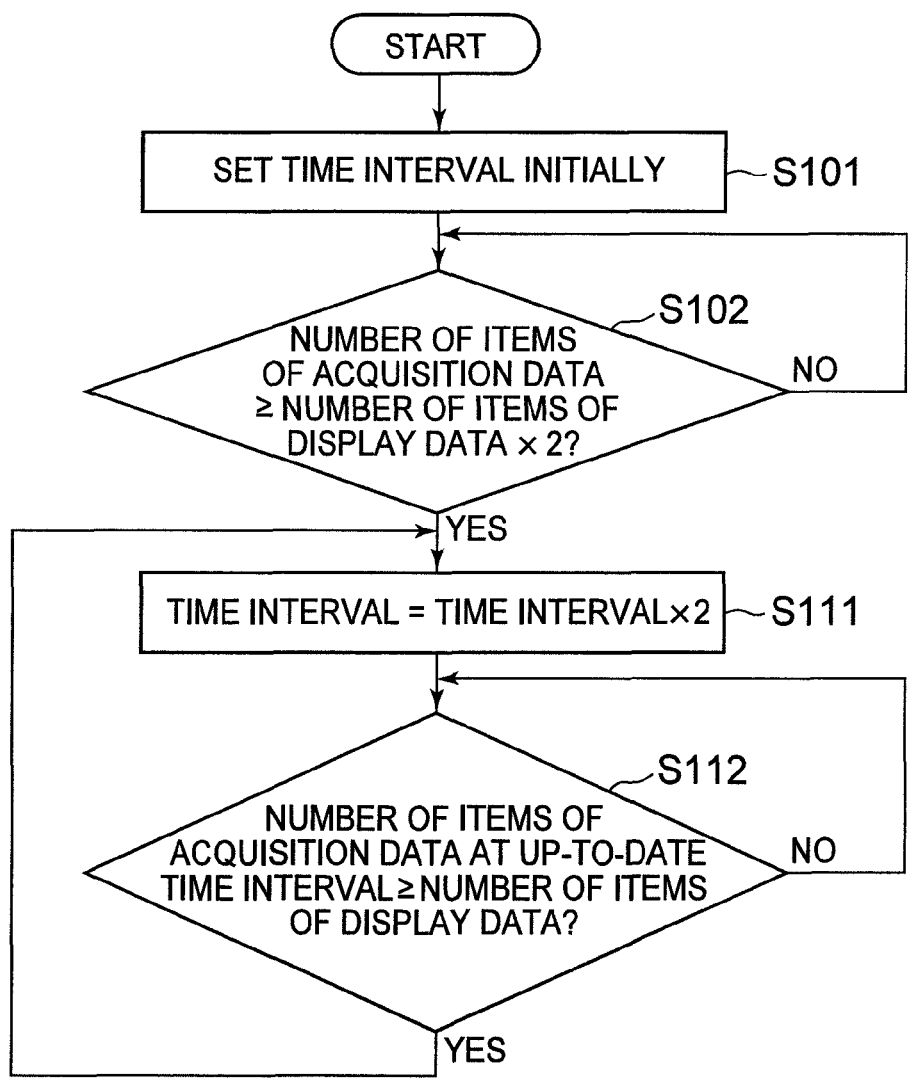
FIG. 8 is a flowchart illustrating the order in which the time interval setting unit performs processing, according to the first embodiment.
Figure 9:
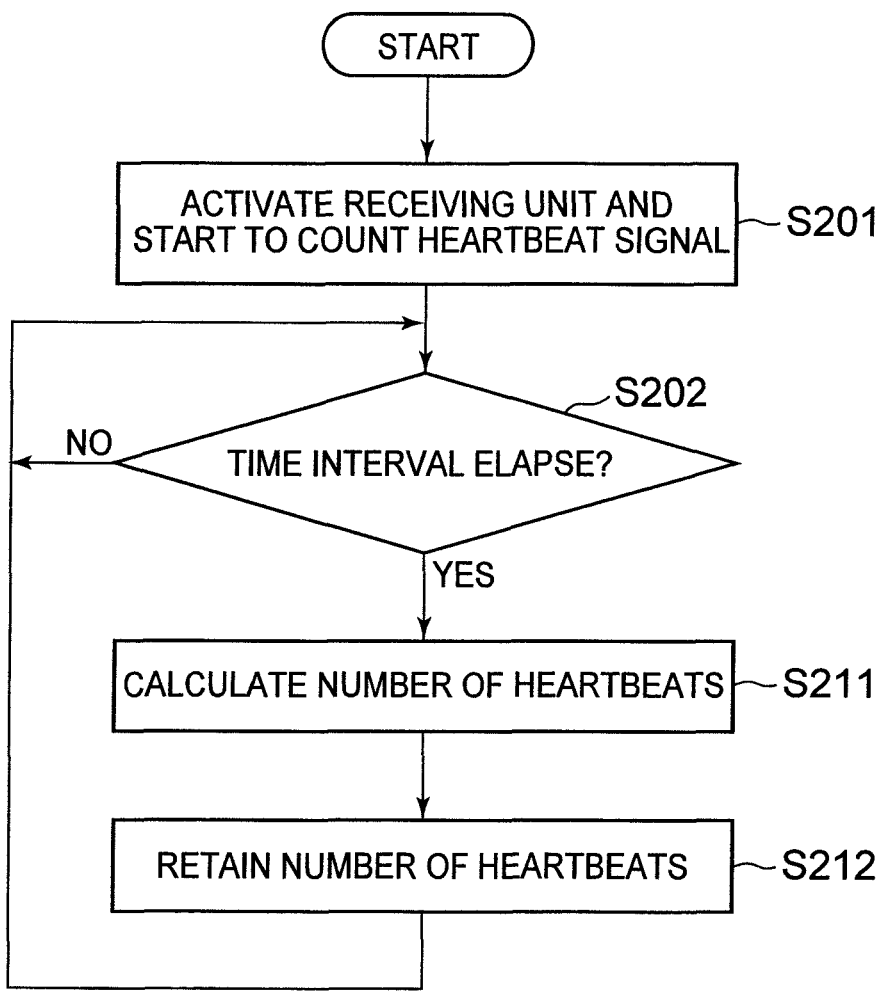
FIG. 9 is a flowchart illustrating the order in which the data acquisition unit performs the processing according to the first embodiment.
Figure 10:
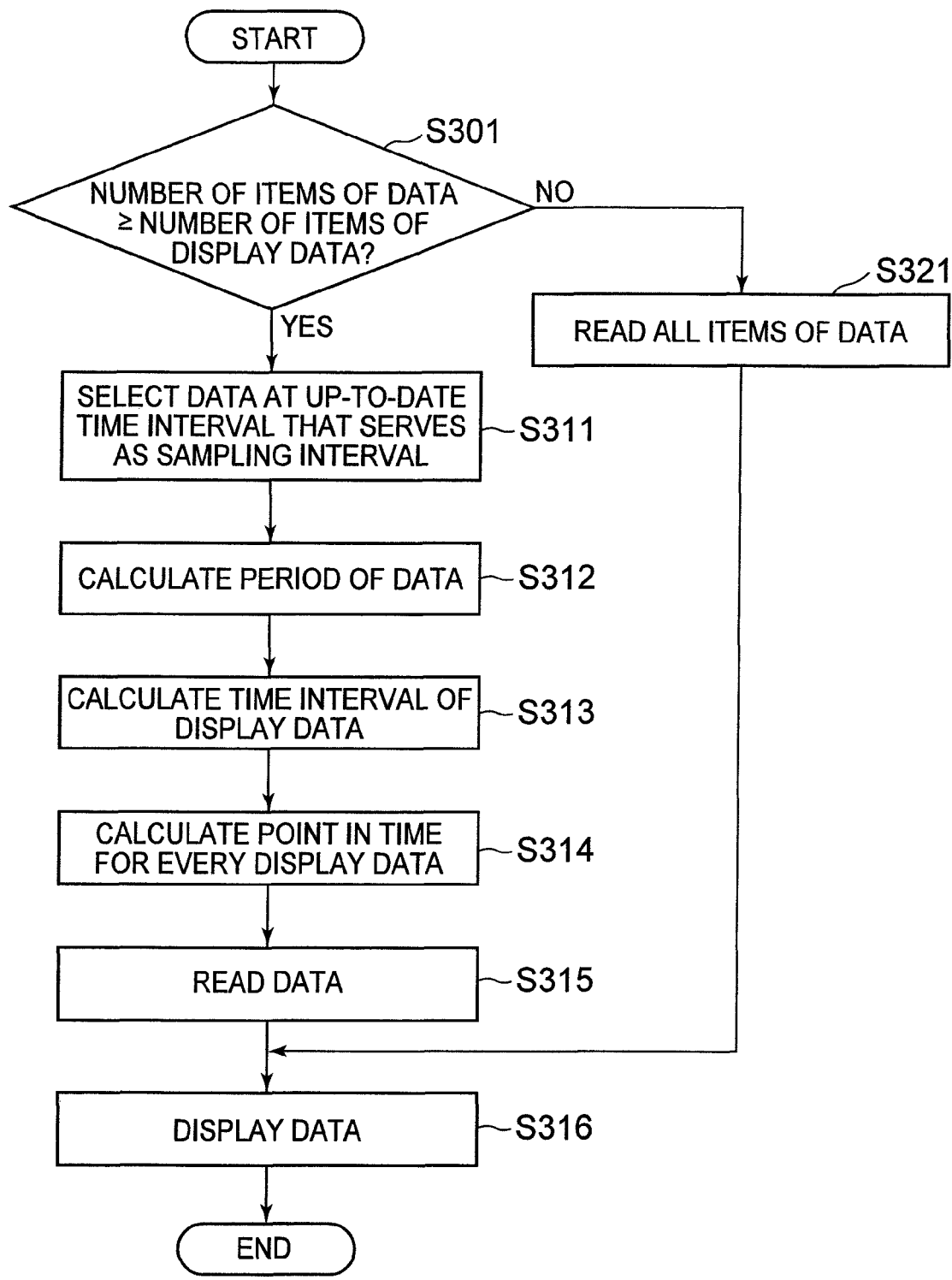
FIG. 10 is a flowchart illustrating the order in which the data extraction unit performs the processing according to the first embodiment.

Next, operation of the running watch 200 is described referring to FIGS. 8 to 10.

FIG. 8 is a flowchart illustrating the order in which the time interval setting unit 220 performs processing. The time interval setting unit 220 performs the processing in FIG. 8 when the running watch 200 measures and stores the number of heartbeats, depending on the user operation.

In the processing in FIG. 8, the time interval setting unit 220 first performs initial time interval setting (Step S101). Specifically, the time interval setting unit 220 sets the time interval as the sampling period with which the data acquisition unit 210 acquires (calculates) the data to an initial value of the time interval (for example, 5 seconds) that is determined in advance.

Next, the time interval setting unit 220 determines whether or not the number of items of data acquired by the data acquisition unit 210 reaches two times the number of items of display data (Step S102). If it is determined that two times the number of items of display data is not reached (Step S102: NO), the processing returns back to Step S102. That is, the time interval setting unit 220 waits for the number of items of data to reach two times the number of items of display data.

On the other hand, if it is determined that the number of items of data acquired by the data acquisition unit 210 reaches two times the number of items of display data (Step S102: YES), the time interval setting unit 220 resets the time interval to two times the time interval (Step S111).

Next, after setting the time interval to the up-to-date time interval, the time interval setting unit 220 determines whether or not the number of items of data acquired by the data acquisition unit 210 reaches the number of items of display data (Step S112). If it is determined that the number of items of display data is not reached (Step S112: NO) the processing returns back to Step S112. That is, the time interval setting unit 220 waits for the number of items of data to reach the number of items of display data.

On the other hand, if it is determined that the number of items of data acquired by the data acquisition unit 210 reaches the number of items of display data after setting the time interval to the up-to-date time interval (Step S112: YES), the processing returns back to Step S111.

In this manner, the time interval setting unit 220 performs the processing in FIG. 8 until the measuring of the number of heartbeats is terminated and gradually increases a setting value of the time interval.

FIG. 9 is a flowchart illustrating the order in which the data acquisition unit 210 performs the processing. The data acquisition unit 210 performs the processing in FIG. 9 when the running watch 200 measures and stores the number of heartbeats, depending on the user operation.

In the processing in FIG. 9, the data acquisition unit 210 first activates the receiving unit 211 and thus receives the heartbeat signal and starts to count the number of the heartbeats (the number of times that the heartbeat signal is received) (Step S201).

Next, the data acquisition unit 210 determines whether or not the time interval that is set by the time interval setting unit 220 elapses after starting the processing in FIG. 9 or after the last time the number of heartbeats is calculated (Step S202).

If it is determined that the time interval does not elapse (Step S202: NO), the processing returns back to Step S202. That is, the data acquisition unit 210 waits for the time interval to elapse.

On the other hand, if it is determined that the time interval elapses (Step S202: YES), the data acquisition unit 210 calculates the number of heartbeats (the number of heartbeats per minute) (Step S211).

Then, the data acquisition unit 210 stores the calculated number of heartbeats in the storage unit 240 through the storage processing unit 230 (Step S212).

Thereafter, the processing returns back to Step 202.

In this manner, the data acquisition unit 210 performs the processing in FIG. 9 until the measuring of the number of heartbeats is terminated and thus calculates the number of heartbeats every time interval and stores the result in the storage unit 240.

FIG. 10 is a flowchart illustrating the order in which the data extraction unit 250 performs the processing. When the user operation that demands the display of the history of the number of heartbeats is performed, the data extraction unit 250 performs the processing in FIG. 10.

However, the timing when the data extraction unit 250 performs the processing in FIG. 10 is not limited to the timing when the user operation is performed. For example, when the running watch 200 measures the number of heartbeats, the data extraction unit 250 may periodically perform the processing in FIG. 10, and the display unit 270 may periodically display the history of the number of heartbeats.

In the processing in FIG. 10, the data extraction unit 250 first determines whether or not the number of items of data stored by the storage unit 240 is equal to or more than the number of items of display data (Step S301).

If it is determined that the number of items of data stored by the storage unit 240 is equal to or more than the number of items of display data (Step S301: YES), the data extraction unit 250 extracts the data stored by the storage unit 240, at the up-to-date time interval, set by the time interval setting unit 220, which serves as the sampling period, as described referring to FIGS. 4 to 7 (Step S311).

Then, the data extraction unit 250 calculates a period for the data that is extracted in Step S311 (Step S312). Specifically, among the items of data that are extracted in Step S311, the data extraction unit 250 subtracts the sampling time in point of the oldest data from the sampling time in point of the up-to-date data (the point in time that is calculated by the data acquisition unit 210).

Next, the data extraction unit 250 calculates the time interval between the items of display data (Step S313). Specifically, the data extraction unit 250 divides the period that is obtained by the calculation in Step S312, by (the number of items of display data—1).

Then, the data extraction unit 250 calculates the point in time that corresponds to each display data (Step S314). Specifically, among the items of data that are extracted in Step S311, if the oldest data is defined as the first data and the up-to-date data is defined as the N-th data, the data extraction unit 250 calculates a point in time T(i) that corresponds to the i-th data (i is an integer that satisfies a condition $1 \leq i \leq N$), based on Expression 1.

$$T(i)=T(1)+(i-1) \cdot D \qquad \text{Expression 1}$$

At this point, a point in time T(1) that corresponds to the first data is set to be the sampling point in time of the first data. Furthermore, a time D indicates the time interval between the items of display data, which is calculated in Step S313.

Next, for every display data, the data extraction unit 250 reads the data at the sampling point in time that is closest to the point in time that corresponds to the display data, from the storage unit 240 through the storage processing unit 230 (Step S315).

Then, the data extraction unit 250 outputs the data that is read from the storage unit 240, to the display control unit 260 and the data is caused to be displayed on the display unit 270 (Step S316).

Thereafter, the processing in FIG. 10 is terminated.

On the other hand, in Step S301, if it is determined that the number of items of data stored by the storage unit 240 is less than a predetermined number of items of data that is set in advance as the number of items of display data (Step S301: NO), the data extraction unit 250 reads all the items of data from the storage unit 240 through the storage processing unit 230 (Step S321).

Thereafter, the processing proceeds to Step S316.

Next, a storage capacity necessary for the storage unit 240 is described referring to FIG. 11.

FIG. 11 is an explanatory diagram illustrating an example of a relationship between data acquirement time and storage capacity. FIG. 11 illustrates the relationship between the data acquirement time and the necessary storage capacity in a case where an initial value of the time interval that is set by the time interval setting unit 220 is 2 seconds, the number of items of display data is 32, and one item of data is stored by 10 bytes.

Referring to a line L11 in FIG. 11, the items of data for one day or more can be stored with the storage capacity of less than 4000 bytes. Furthermore, referring to a line L12 in FIG. 11, the items of data for 6 days or more can be stored with the storage capacity of less than 4500 bytes.

In this manner, in the running watch 200, the items of data for a long period of time can be stored with less storage capacity.

As described above, the time interval setting unit 220 sets the time interval that depends on the number of items of data stored by the storage unit 240. Then, among the items of data acquired by the data acquisition unit 210, the storage processing unit 230 stores the data in the storage unit 240 at every time interval that is set by the time interval setting unit 220. In this manner, the storage unit 240 retains the data at the time interval that depends on the data acquirement time.

At this point, the data extraction unit 250 extracts the data by the number of items of data that depends on a predetermined number of items of display data, from the items of data stored by the storage unit 240. Accordingly, when the time interval setting unit 220 updates the time interval, it is not necessary to perform the subsampling or the compression on the data stored by the storage unit 240. In this respect, the running watch 200 (the storage processing unit 230) can retain the data at the time interval that depends on the data acquirement time, with less processing load.

Furthermore, CPU load and an increase in memory region can be prevented due to the data subsampling or the data compression that is performed when the number of items of data stored by the storage unit 240 is increased, in that it is not necessary to perform the subsampling or the compression on the data stored by the storage unit 240.

Moreover, a decrease in the number of times that the data writing is performed on the storage unit 240 causes no problem in that it is not necessary to perform the subsampling or the compression on the data stored by the storage unit 240. Therefore, although the storage unit 240 is realized using electrically erasable programmable read-only memory (EEPROM) or flash memory, the number of times that the writing is performed can be prevented from reaching the limited number of times for a short period of time and thus the product life of the running watch 200 can be prevented from being shortened.

Furthermore, if the time interval setting unit 220 itself sets the up-to-date time interval and then the number of items of data that the storage processing unit 230 stores in the storage unit 240 at every up-to-date time interval reaches a predetermined number, the time interval setting unit 220 sets the time interval as being increased.

In this manner, the time interval setting unit 220 sets the time interval of the data to be stored in the storage unit 240 as being further increased, depending on an increase in the number of items of data stored by the storage unit 240 and thus can alleviate the increase in the number of items of data.

Furthermore, when the time interval is the initially set time interval, if the number of items of data that the storage processing unit 230 stores in the storage unit 240 at every initially set time interval reaches two times the number of items of display data, the time interval setting unit 220 resets the time interval to two times the time interval.

In this manner, the time interval setting unit 220 maintains the initially set time interval and thus stores the items of data the number of which is equal to or more than the number of items of display data, in the storage unit 240. Thus, the display unit 270 can display the data by the number of items of display data. Furthermore, when the time interval setting unit 220 resets the time interval to two times the time interval, the storage unit 240 already stores the items of data with the reset time interval, by the number of items of display data. Therefore, the display unit 270 can display the data by the number of items of display data also after the time interval resetting.

Furthermore, when the time interval is the reset time interval, if the number of items of data that the storage processing unit 230 stores the data at every up-to-date time interval in the storage unit 240 reaches the number of items of display data, the time interval setting unit 220 resets the time interval to two times the up-to-date time interval.

Accordingly, when the time interval setting unit 220 resets the time interval to two times the time interval, the storage unit 240 already stores the items of data with the reset time interval, by the number of items of display data. Therefore, the display unit 270 can display the data by the number of items of display data also after the time interval resetting.

Furthermore, the data extraction unit 250 calculates the point in time of each display data in a case where the time intervals between the items of display data are equal and reads the data at the sampling point in time that is closest to the calculated point in time, as the display data, from the storage unit 240.

Accordingly, the data extraction unit 250 can extract the data with the near-uniformity time interval, as the display data.

Furthermore, the data extraction unit 250 calculates the point in time of each display data in a case where the time intervals between the items of display data are equal. And for every display data, the data extraction unit 250 reads one item of data at the sampling point in time that is closest to the calculated point in time, before the calculated point in time and reads one item of data at the sampling point in time that is closest to the calculated point in time, after the calculated point in time, and sets an average value of the two read items of data as a value of the display data.

Accordingly, although there is a comparatively big difference between the calculated point in time and the sampling point in time of the data actually stored by the storage unit 240, the data extraction unit 250 performs interpolation by averaging and thus can acquire the data that is close to the data with the calculated point in time.

Furthermore, the data acquisition unit 210 acquires the data at the time interval, set by the time interval setting unit 220, which serves as the sampling period.

The data acquisition unit 210 acquires the data in this manner, depending on the time interval set by the time interval setting unit 220, and thus the storage processing unit 230 may store all the items of data acquired by the data acquisition unit 210 in the storage unit 240 and does not have to perform subsampling or compression on the data. In this respect, an increase in the processing load on the storage processing unit 230 can be suppressed.

In addition, the data acquisition unit 210 calculates the number of heartbeats (the number of heartbeats per minute) with the constant sampling period regardless of the time interval resetting by the time interval setting unit 220, and may acquire the data at every time interval by averaging the number of heartbeats calculated for a given period of time at every time interval that is set by the time interval setting unit 220.

In this case, although an error temporarily occurs in the number of heartbeats, such as when noise mixes with the heartbeat signal from the chest strap 100 (the transmission unit 120), because the data acquisition unit 210 calculates an average of the number of heartbeats, an effect of the error can be reduced.

In addition, the display data and the number of items of display data according to the first embodiment are examples of representative data and the number of items of representative data according to a second embodiment, respectively.

In addition, the simulation studies by the inventor of the present invention showed that a form of the graph displayed when applying the present invention is close to a form of the graph on which raw data is plotted.

FIG. 12 is a graph illustrating a result of the simulation showing the number of heartbeats according to the present embodiment.

In FIG. 12, a line L21 indicates simulation values of the actual heart rate (the number of heartbeats per minute).

Furthermore, a line L22 indicates values that are sampled from the simulation values of the actual heart rate every five seconds. The values indicated by the line L22 corresponds to the example of the display data on the display unit 270 in a state where the time interval setting unit 220 sets the time interval to an initial setting value of five seconds.

Furthermore, a line L23 indicates values that are sampled from the simulation values of the actual heart rate every ten seconds. The values indicated by the line L23 corresponds to the example of the display data on the display unit 270 in a state where the time interval setting unit 220 updates the time interval to ten seconds from the initial setting value of five seconds.

Furthermore, a line L24 indicates values that are sampled from the simulation values of the actual heart rate every twenty seconds. The values indicated by the line L24 corresponds to the example of the display data on the display unit 270 in a state where the time interval setting unit 220 updates the time interval two times from the initial setting value of five seconds, resulting in the time interval being 20 seconds.

It is indicated from FIG. 12 that the form of any one of the lines L22 to L24, when viewed as a whole, is the same as the form of the line L21. Accordingly, it is confirmed that the form of the graph when applying the present invention is close to the graph on which the raw data is plotted.

Second Embodiment

Figure 13:
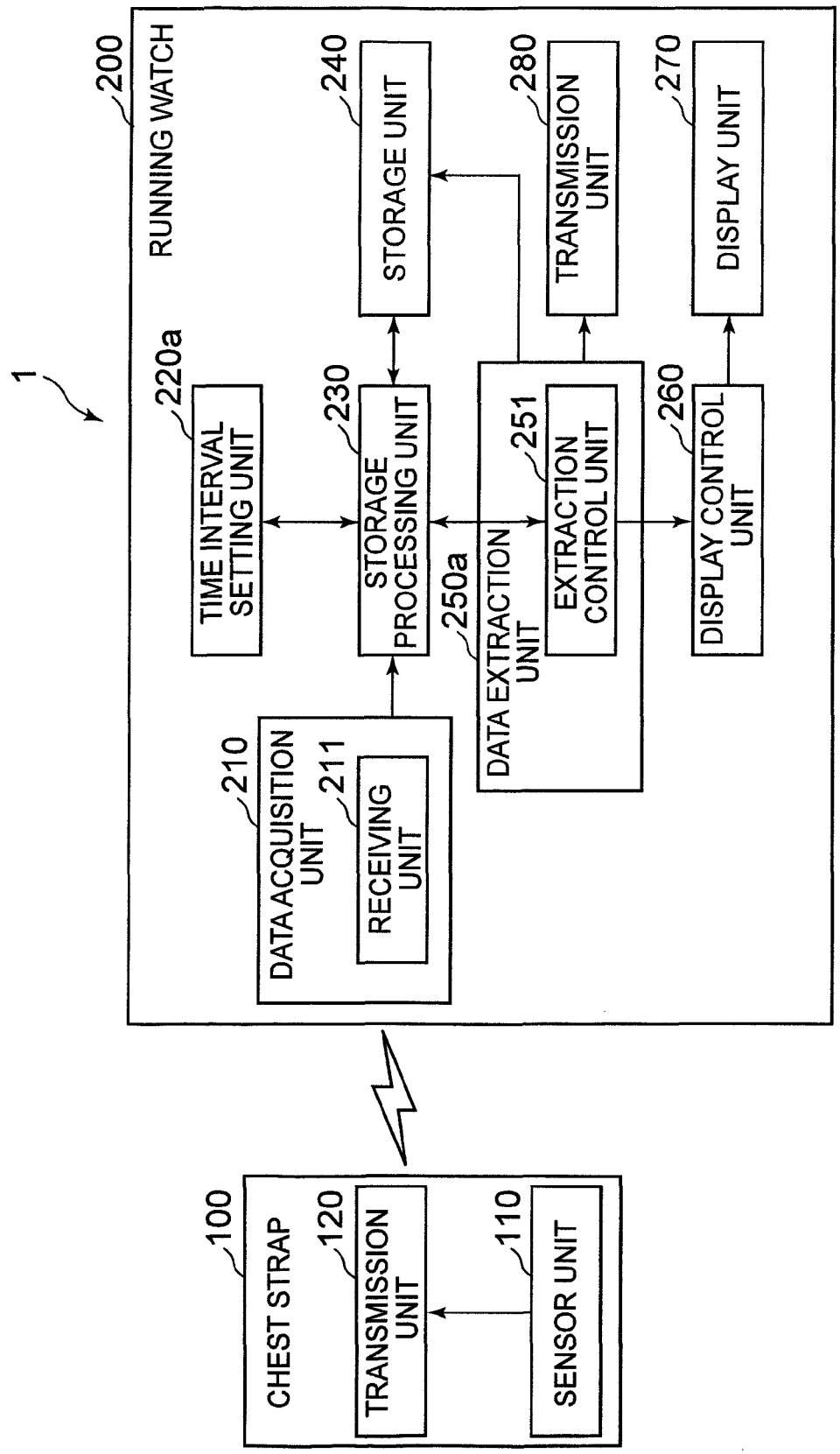
FIG. 13 is a schematic configuration diagram illustrating a system configuration of a running watch system according to a second embodiment of the present invention.

Subsequently, a second embodiment is described in detail. FIG. 13 is a schematic block diagram illustrating a functional configuration of a running watch system 1 according to the second embodiment. In FIG. 13, the same reference numerals as those in FIG. 2 are used in a configuration that is common to the first embodiment, and a description of the configuration is omitted. The running watch system 1 includes a chest strap 100 and a running watch 200. The running watch 200 includes a data acquisition unit 210, a time interval setting unit 220a, a storage processing unit 230, a storage unit 240, a data extraction unit 250a, a display control unit 260, a display unit 270, and a transmission unit 280. The data acquisition unit 210 includes a receiving unit 211. The data extraction unit 250a includes an extraction control unit 251.

When a time interval is an initially set time interval, if the number of items of data that the storage processing unit 230 stores in the storage unit 240 at every initially set time interval reaches the predetermined constant number times the number of items of representative data, the time interval setting unit 220a resets the time interval to the predetermined constant number times the time interval. The representative data is one item of data that belongs to a group of items of representative data indicating a tendency of the data, which is usable for other than the purpose of display on the display unit 270, such as for a statistical analysis performed by an analyzing server described below. Specifically, one example of the representative data is the data that, as illustrated in FIG. 3C according to the first embodiment, is extracted at the up-to-date time interval, set by the time interval setting unit 220, which serves as the sampling period. The data that is extracted at every predetermined period T1 that is different from the sampling period, or the data that is extracted from only the items of data that are present during the period during which the receiving unit 211 receives the data in the case where the data relates to the heartbeat corresponds to another example of the representative data. The number of items of representative data is one example of a predetermined number of items of data, in the claims. The number of items of representative data, for example, is a constant number that is set in advance in the data extraction unit 250a, and the display unit 270 according to the second embodiment reads the data by the number of items of representative data that serves as the number of items of display data. In addition, the predetermined constant number is an integer such as 2 or 3. Furthermore, the initially set time interval, for example, may be registered in advance with the time interval setting unit 220a, be set later by the user, and be calculated depending on an amount of unoccupied space in data regions of the storage unit 240.

The data extraction unit 250a extracts the representative data from the items of data stored by the storage unit 240. Then, the data extraction unit 250a displays the extracted representative data on the display unit 270. Furthermore, the data extraction unit 250a stores the extracted representative data in the storage unit 240. Furthermore, when a capacity of a storage region of the storage unit 240 is decreased to less than a predetermined threshold, the data extraction unit 250a notifies the user that the storage region is decreased, and depending on the user operation responding to the notification, the transmission unit 280 described below transmits the representative data to an external analyzing server or cloud server and deletes the transmitted representative data from the storage unit 240. Accordingly, the running watch 200 can record the user data over a longer period of time.

The extraction control unit 251 controls the data extraction unit 250a in such a manner that the representative data is extracted at a predetermined timing from the items of data stored by the storage unit 240. The predetermined timing, for example, is a timing when the transmission unit 280 described below transmits the representative data to the analyzing server that performs the statistical analysis and to the cloud server, a timing when a predetermined period T2 elapses, or a timing when the receiving unit 211 terminates the receiving because the measuring time elapses. By causing the data extraction unit 250a to perform the extraction at such timings, the extraction control unit 251 can extract the representative data when a CPU utilization rate is decreased, for example, after terminating the measuring, without having to change the load on the CPU in the middle of acquiring the data.

The transmission unit 280 wirelessly transmits the representative data extracted by the data extraction unit 250a to the external analyzing server or cloud server depending on the user operation. In addition, the transmission unit 280 may transmit the representative data each time a predetermined period T3 elapses instead of transmitting the representative data depending on the user operation. Furthermore, the transmission unit 280 may transmit the display data instead of the representative data. Furthermore, information relating to a sampling interval or information to the number of items of data may be included in the data that is transmitted.

Figure 14A:
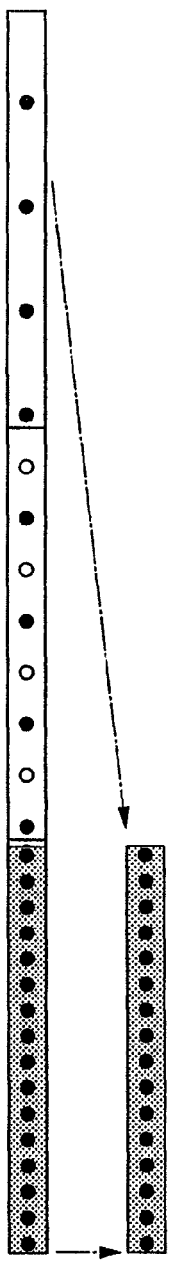
FIGS. 14A and 14B are explanatory diagrams, each illustrating one example of the data that is present within a storage region when a data extraction unit stores representative data in a storage unit, according to the second embodiment of the present invention.
Figure 14B:
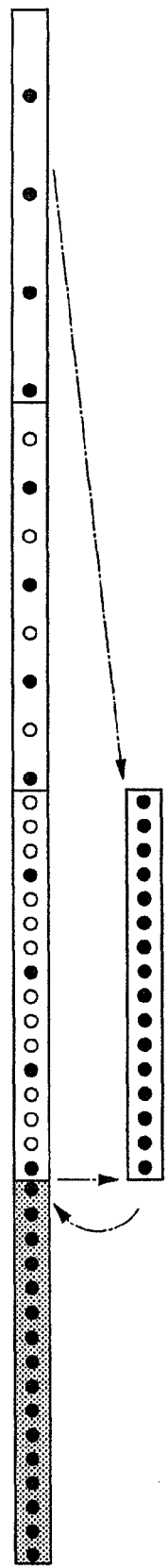

At this point, the data that is present within the storage region when the data extraction unit 250a stores the representative data in the storage unit 240 is described referring to FIGS. 14A and 14B. As illustrated in FIG. 14A, the data extraction unit 250a overwrites the original data stored in the storage region of the storage unit 240, which is used when extracting the representative data, with the representative data for storage. In addition, the data extraction unit 250a may store the display data displayed on the display unit 270 in the storage unit 240, instead of storing the representative data. Furthermore, as illustrated in FIG. 14B, after storing the representative data by overwriting, the data extraction unit 250a stores the data newly acquired by the data acquisition unit 210 on the storage region other than the region in which the representative data is stored. Then, the data extraction unit 250a repeatedly extracts the representative data from the newly stored items of data again and stores the representative data by overwriting. In addition, when storing the extracted representative data in the storage unit 240, the data extraction unit 250*a* may delete the original data from the storage region of storage unit 240, in which the original data used when extracting the representative data is stored, and may store the representative data in the storage region from which the original data is deleted, instead of storing the representative data by overwriting.

At this point, the data that is present within the storage region when the data extraction unit 250*a* stores the display data displayed on the display unit 270 in the storage unit 240 instead of storing the representative data is described referring to FIGS. 15A and 15B. As illustrated in FIG. 15A, after extracting the representative data, the data extraction unit 250*a* displays the representative data on the display unit 270 and stores the displayed data in the storage region in which the original data is stored, by overwriting. Furthermore, as illustrated in FIG. 15B, after storing the displayed data by overwriting, the data extraction unit 250*a* stores the data newly acquired by the data acquisition unit 210 in the storage region other than the region in which the display data is stored. Then, the data extraction unit 250*a* repeatedly extracts the representative data from the newly stored items of data again and stores the displayed data by overwriting.

In this manner, in the running watch 200 according to the second embodiment, when the number of items of data that the storage processing unit 230 stores in the storage unit 240 at every initially set time interval reaches predetermined constant number times the number of items of representative data, the time interval setting unit 220*a* resets the time interval to the predetermined constant number times the time interval. As a result, the running watch 200 according to the second embodiment can obtain the same effect as in the first embodiment. Furthermore, the running watch 200 controls the data extraction unit 250*a* in such a manner that the data extraction unit 250*a* extracts the representative data at a predetermined timing from the items of data stored by the storage unit 240. Therefore, the running watch 200 can extract the representative data when the CPU utilization rate is decreased, for example, after terminating the measuring, without having to change the load on the CPU in the middle of performing the measuring. Accordingly, the running watch 200 according to the second embodiment can have the same CPU responsiveness as the running watch 200 according to the first embodiment and thus can maintain the user's convenience.

Furthermore, the data extraction unit 250*a* stores the extracted representative data in the storage unit 240. Therefore, in the running watch 200, because it is necessary to secure the storage region, separately from the original data acquired by the data acquisition unit 210 in order to store the representative data, the time for which the data can be retained is gradually decreased. However, because of this, the running watch 200 is considerably efficient in retaining the multiple items of data and the storage region can be used. Furthermore, because the transmission unit 280 transmits the representative data to the analyzing server or the cloud server, a communication speed can be improved compared to the transmission of the original data acquired by the data acquisition unit 210.

In addition, in order to perform the processing by each unit, a program for realizing functions of all or some of the data acquisition unit 210, the time interval setting unit 220, the storage processing unit 230, the data extraction unit 250, the data extraction unit 250*a*, and the display control unit 260 may be recorded on a computer-readable recording medium, and a computer system may be caused to read and execute the program recorded on this recording medium. In addition, the "computer system" here is defined as including an OS and hardware units such as a peripheral device.

Furthermore, if the WWW system is used, the "computer system" is defined as including an environment in which webpages are provided (or an environment in which the display is available).

Furthermore, the "computer-readable recording medium" refers to a portable medium such as a flexible disk, a magneto-optical disk, ROM, and CD-ROM, and a storage device such as a hard disk that is built into the computer system. Moreover, the "computer-readable recording medium" is defined as including whatever dynamically includes the program for a short period of time, such as a communication line that is used when transmitting the program over a network such as the Internet or over a communication circuit such as a telephone circuit and as including whatever retains the program for a constant period of time, such as volatile memory within the computer system, which functions as a server or a client in the case of including the program dynamically. Furthermore, the program may be one for realizing some of the functions described above and additionally may be one that can realize the functions described above in combination with a program that is already recorded in the computer system.

The embodiments according to the present invention are described above in detail referring to the drawings, but the specific configuration is not limited to the embodiments and includes an amendment to a design that falls within a scope not deviating from the gist of the present invention.

What is claimed is:

1. An electronic device comprising:
   a data acquisition unit that acquires data periodically;
   a storage unit that stores at least one part of the items of data acquired by the data acquisition unit;
   a time interval setting unit that sets a time interval that depends on the number of items of data stored by the storage unit;
   a storage processing unit that stores the data in the storage unit at every time interval that is set by the time interval setting unit, among the items of data acquired by the data acquisition unit; and
   a data extraction unit that extracts the data as representative data by a predetermined number of items of data from the items of data stored by the storage unit.

2. The electronic device according to claim 1, further comprising:
   a transmission unit that transmits the representative data extracted by the data extraction unit to an external server.

3. The electronic device according to claim 1, further comprising:
   a display unit that displays the data by the predetermined number of items of data, based on the representative data extracted by the data extraction unit.

4. The electronic device according to claim 2, further comprising:
   a display unit that displays the data by the predetermined number of items of data, based on the representative data extracted by the data extraction unit.

5. The electronic device according to claim 2,
   wherein the data extraction unit extracts the representative data at a predetermined timing, and
   wherein the predetermined timing is a timing when the transmission unit transmits the representative data to the external server or is a timing when the data acquisition unit terminates the acquiring of the data.

6. The electronic device according to claim 4,
wherein the data extraction unit extracts the representative data at a predetermined timing, and
wherein the predetermined timing is a timing when the transmission unit transmits the representative data to the external server or is a timing when the data acquisition unit terminates the acquiring of the data.

7. The electronic device according to claim 1,
wherein if the time interval setting unit sets the most recent time interval and then the number of items of data that the storage processing unit stores in the storage unit at every time interval that is set most recently reaches the predetermined number of items of data, the time interval setting unit sets the time interval as being further increased.

8. The electronic device according to claim 2,
wherein if the time interval setting unit sets the most recent time interval and then the number of items of data that the storage processing unit stores in the storage unit at every time interval that is set most recently reaches the predetermined number of items of data, the time interval setting unit sets the time interval as being further increased.

9. The electronic device according to claim 3,
wherein if the time interval setting unit sets the most recent time interval and then the number of items of data that the storage processing unit stores in the storage unit at every time interval that is set most recently reaches the predetermined number of items of data, the time interval setting unit sets the time interval as being further increased.

10. The electronic device according to claim 4,
wherein if the time interval setting unit sets the most recent time interval and then the number of items of data that the storage processing unit stores in the storage unit at every time interval that is set most recently reaches the predetermined number of items of data, the time interval setting unit sets the time interval as being further increased.

11. The electronic device according to claim 5,
wherein if the time interval setting unit sets the most recent time interval and then the number of items of data that the storage processing unit stores in the storage unit at every time interval that is set most recently reaches the predetermined number of items of data, the time interval setting unit sets the time interval as being further increased.

12. The electronic device according to claim 6,
wherein if the time interval setting unit sets the most recent time interval and then the number of items of data that the storage processing unit stores in the storage unit at every time interval that is set most recently reaches the predetermined number of items of data, the time interval setting unit sets the time interval as being further increased.

13. The electronic device according to claim 1,
wherein when the time interval is an initially set time interval, if the number of items of data that the storage processing unit stores in the storage unit at every initially set time interval reaches a value that is obtained by multiplying the predetermined number of items of data by a predetermined value, the time interval setting unit resets the time interval to a time interval that is obtained by multiplying the time interval by predetermined value, and
wherein when the time interval is the reset time interval, if the number of items of data that the storage processing unit stores in the storage unit at every time interval that is set most recently reaches the predetermined number of items of data, the time interval setting unit resets the time interval to a time interval that is obtained by additionally multiplying the time interval, set most recently, by the predetermined value.

14. The electronic device according to claim 2,
wherein when the time interval is an initially set time interval, if the number of items of data that the storage processing unit stores in the storage unit at every initially set time interval reaches a value that is obtained by multiplying the predetermined number of items of data by a predetermined value, the time interval setting unit resets the time interval to a time interval that is obtained by multiplying the time interval by predetermined value, and
wherein when the time interval is the reset time interval, if the number of items of data that the storage processing unit stores in the storage unit at every time interval that is set most recently reaches the predetermined number of items of data, the time interval setting unit resets the time interval to a time interval that is obtained by additionally multiplying the time interval, set most recently, by the predetermined value.

15. The electronic device according to claim 3,
wherein when the time interval is an initially set time interval, if the number of items of data that the storage processing unit stores in the storage unit at every initially set time interval reaches a value that is obtained by multiplying the predetermined number of items of data by a predetermined value, the time interval setting unit resets the time interval to a time interval that is obtained by multiplying the time interval by predetermined value, and
wherein when the time interval is the reset time interval, if the number of items of data that the storage processing unit stores in the storage unit at every time interval that is set most recently reaches the predetermined number of items of data, the time interval setting unit resets the time interval to a time interval that is obtained by additionally multiplying the time interval, set most recently, by the predetermined value.

16. The electronic device according to claim 1,
wherein the data extraction unit calculates a point in time that corresponds to each data in a case where the time intervals between the items of data are equal, based on the predetermined number of items of data, and reads the data at a sampling point in time that is closest to the calculated point in time, as representative data, from the storage unit.

17. The electronic device according to claim 1,
wherein the data extraction unit calculates a point in time that corresponds to each data in a case where the time intervals between the items of data are equal, based on the predetermined number of items of data, reads one item of data at a sampling point in time that is closest to the calculated point in time before the calculated point in time and reads one item of data at the sampling point in time that is closest to the calculated point in time after the calculated point in time, from the items of representative data, and sets an average value of the read two items of data as a new value of the representative data.

18. The electronic device according to claim 1,
wherein the data acquisition unit acquires the data at the time interval, set by the time interval setting unit, which serves as a sampling period.

19. A method of extracting data for use in an electronic device including a storage unit that stores the data, comprising:
- periodically acquiring the data;
- setting a time interval that depends on the number of items of data that is stored by the storage unit;
- storing the data in the storage unit at every time interval that is set in the setting of the time interval, among the items of data acquired in the periodical acquiring of the data; and
- causing a data extraction unit to extract the data as a representative data by a predetermined number of items of data from the items of data stored by the storage unit.

20. A program for causing a computer that controls an electronic device including a storage unit that stores the data to execute a process, the process comprising:
- periodically acquiring the data;
- setting a time interval that depends on the number of items of data that is stored by the storage unit;
- storing the data in the storage unit at every time interval that is set in the setting of the time interval, among the items of data acquired in the periodical acquiring of the data; and
- causing a data extraction unit to extract the data as a representative data by a predetermined number of items of data from the items of data stored by the storage unit.

* * * * *